(12) United States Patent
Takehara

(10) Patent No.: US 7,844,325 B2
(45) Date of Patent: Nov. 30, 2010

(54) BIOELECTRICITY IMPEDANCE MEASURING DEVICE, A MALNUTRITION MEASUREMENT SYSTEM, A MALNUTRITION MEASUREMENT METHOD

(75) Inventor: Tomoko Takehara, Osaka (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 12/155,434

(22) Filed: Jun. 4, 2008

(65) Prior Publication Data

US 2008/0306400 A1    Dec. 11, 2008

(30) Foreign Application Priority Data

Jun. 6, 2007    (JP) .............................. 2007-150323

(51) Int. Cl.
*A61B 5/06*    (2006.01)
(52) U.S. Cl. ..................................... 600/547
(58) Field of Classification Search .................. 600/547
See application file for complete search history.

(56) References Cited

U.S. PATENT DOCUMENTS

| | | | |
|---|---|---|---|
| 6,256,532 | B1 | 7/2001 | Cha |
| 6,714,814 | B2 * | 3/2004 | Yamada et al. ............. 600/547 |
| 2004/0082877 | A1 * | 4/2004 | Kouou et al. ............... 600/547 |
| 2004/0167423 | A1 * | 8/2004 | Pillon et al. ................. 600/547 |

FOREIGN PATENT DOCUMENTS

| | | |
|---|---|---|
| EP | 1138259 | 10/2001 |
| JP | 2001-299717 | 10/2001 |

OTHER PUBLICATIONS

Chumlea et al., Mechanical and physiologic modifiers and bioelectrical impedance spectrum determinants of body composition, 1996, American Journal of Clinical Nutrition, 64:413S-422S.*
Dung et al., Impedance index or standard anthropometric measurements, which is the better variable for predicting fat-free mass in sick children?, published online May 24 2007, Acta Paediatrica, 96, 869-873.*
Wirth R. et al: Bioelectric impedance analysis in the diagnosis of malnutrition. DA, vol. 38, No. 5, Oct. 1, 2005, pp. 315-321. XPO019382528. ISSN: 1435-1269.

* cited by examiner

*Primary Examiner*—Max Hindenburg
*Assistant Examiner*—Emily M Lloyd
(74) *Attorney, Agent, or Firm*—Paul F. Neils, Esq.; Akerman Senterfitt

(57) ABSTRACT

A bioelectricity impedance measuring device includes a contact surface capable of being placed on a part of the body, a gripper which is formed to be easily grasped by a single hand, and electrodes on the contact surface. In addition, the bioelectricity impedance measuring device further includes a malnutrition measuring device which measures malnutrition. An operation and control device measures Phase angle theta and/or an RcXc ratio, and measures a nutrient state. The malnutrition measuring device measures the state of malnutrition from a value of Phase angle theta. A display shows the results of measurement with a bar classified by display of a color. In addition, the operation and control device further measures muscular volume. The operation and control device, by being capable of being provided data or regression, can also measure muscular volume for a child aged 5 or younger or an adult aged 60 or older.

11 Claims, 12 Drawing Sheets

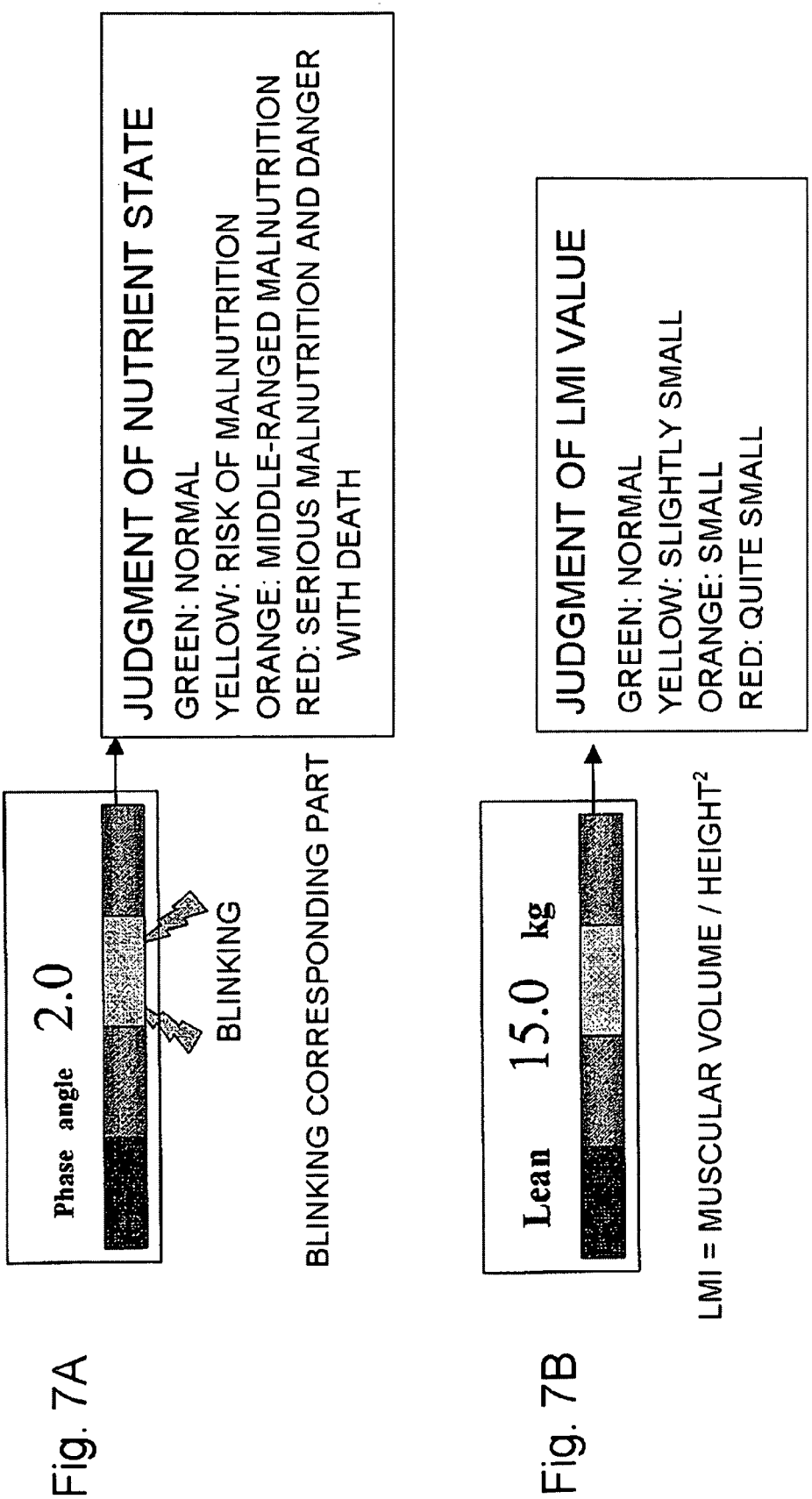

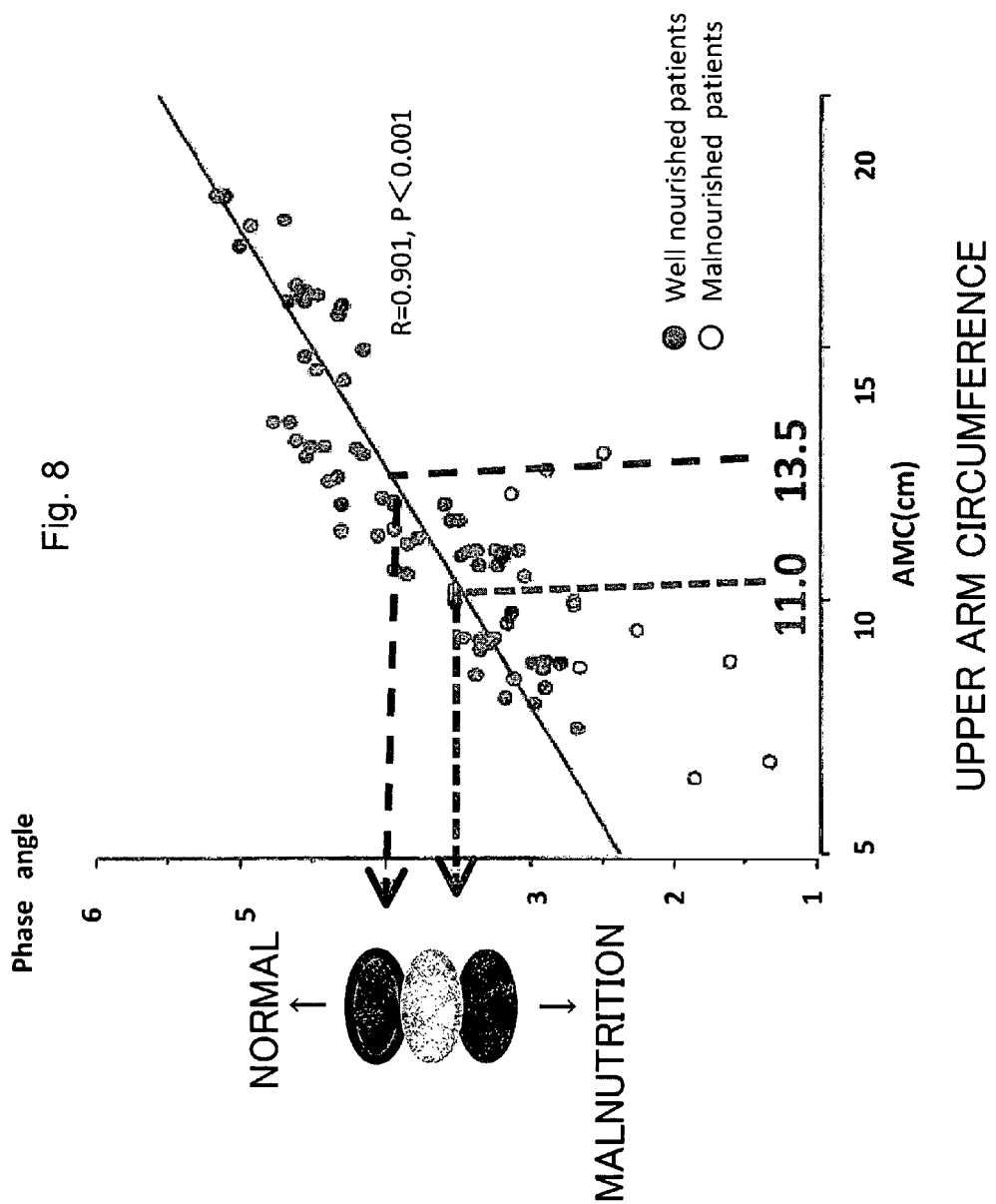

BIOELECTRICITY IMPEDANCE MEASURING DEVICE, A MALNUTRITION MEASUREMENT SYSTEM, A MALNUTRITION MEASUREMENT METHOD

CROSS REFERENCE OF THE INVENTION

The present application claims the benefit of the filing date of Japanese Patent Application No. 2007-150323 filed Jun. 6, 2007.

BACKGROUND OF THE INVENTION

1. Field of the Invention

Especially this invention relates to the bioelectricity impedance measuring device, malnutrition measurement system, and malnutrition measuring method which can measure malnutrition.

2. Background of the Invention

Also in recent years, there are 60 million or more children under 5 years old that suffer from malnutrition in the world, and 5 million people die every year because of the poverty in developing countries and abuse at home, anorexia, or the like in advanced nations.

The demand of nutrition and supply which is needed to avoid malnutrition for growth of the body, maintenance, and activity are defined as a state out of balance.

In order to measure this malnutrition, the MUAC method which measures an upper arm circumference exists.

(see the work by Doctors Without Borders, "a malnutrition guide (introductory edition)".

Although the MUAC method can measure malnutrition simply for a child aged 5 and below, an upper arm circumference changes in size between a shoulder and an elbow, and since an error made by the person measuring is also large, there is a problem that repeatability is not so high.

Therefore, a demand exist for an equipment that can carry out the measurement of malnutrition accurately with high repeatability.

Here, a former body composition monitor by a bioelectricity impedance measuring device currently used can measure accurately weight, amount of body fat, and muscular volume.

However, the body composition monitor that measures in a standing position is in use, and the object which is hard to hold a standing position posture according to malnutrition and illness cannot be measured.

In the case of the body composition monitor of a standing position, it cannot be used for an object living with bare feet and the sole has keratinized.

Therefore, as a bioelectricity impedance measuring device which can be used for objects other than a standing position, for example, it is possible to use the body composition monitor, which pushes an electrode against the upper arm part, as indicated to patent document 1 (hereafter, it is called to conventional technology 1.)

[Patent document 1]
  JPA 2001-299717

DESCRIPTION OF THE INVENTION

Problem(s) to be Solved by the Invention

However, formerly, since the body composition monitor of patent documents 1 was targeting an adult about measurement of amount of body fat and muscular volume, it was not able to measure infants.

Also, it had a problem that amount of body fat and muscular volume might not always correlate to acute malnutrition by starvation. In cibophobia and anorexia nervosa, there was a problem that measuring weight and looking at amount of body fat puts stress on a patient.

For this reason, the bioelectricity impedance measuring device for which measurement is possible with the different scale involving malnutrition was desired.

This invention is made in view of such a situation, and makes it a subject to address an above-mentioned subject.

SUMMARY OF THE INVENTION

A bioelectricity impedance measuring device of this invention is provided with a malnutrition measuring means which is a bioelectricity impedance measuring device which comprises a housing with a contact surface capable of being placed on a part of the body, and a gripper, and comprises electrodes facing the same direction from the contact surface of the housing, and measures malnutrition.

A bioelectricity impedance measuring device of this invention is comprised so that a concave might be formed with the gripper, and the contact surface might be projected from both ends of the gripper to a uniform direction and it might have an electrode. A bioelectricity impedance measuring device of this invention is characterized by the malnutrition measuring means being a means which measures Phase angle theta and/or a RcXc ratio, and measures a nutrient state.

A bioelectricity impedance measuring device of this invention is provided with a means by which the malnutrition measuring means judges a state of malnutrition from a value of Phase angle theta.

A bioelectricity impedance measuring device of this invention is provided with a means to display the judged result with a bar classified by color.

A bioelectricity impedance measuring device of this invention is further provided with a muscular volume measuring means which measures muscular volume.

As for a bioelectricity impedance measuring device of this invention, the muscular volume measuring means is provided with data for measurement of muscular volume to a child aged 5 and below or an old man aged 60 and over.

The bioelectricity impedance measuring device of this invention can carry out measurement of a nutrient state, and/or measurement of muscular volume with sex and/or height, and an individual parameter of age.

A bioelectricity impedance measuring device of this invention is characterized by being held and carried with a single hand, and it being available to measure malnutrition.

A bioelectricity impedance measurement system of this invention is a malnutrition measurement system containing a bioelectricity impedance measuring device which comprises a housing with a contact surface capable of being placed on a part of the body, and a gripper, and comprises a uniform direction with an electrode from both ends of the gripper, and other computers, and data being received from a bioelectricity impedance measuring device provided with a malnutrition measuring means which measures malnutrition, and the impedance measurement device, and it having a memory measure which can memorize temporal data via communication.

A malnutrition measuring method of this invention judges a nutrient state from Phase angle theta and/or a RcXc ratio with an electrical impedance measuring device which can be carried, measures muscular volume simultaneously, and measures a state of malnutrition.

EFFECT OF THE INVENTION

According to this invention, the bioelectricity impedance measuring device which can measure malnutrition can be provided.

BRIEF DESCRIPTION OF THE DRAWINGS

FIG. 7, including FIGS. 7A and 7B, is a conceptual diagram showing the example of an indication as a result of measurement of the malnutrition and measurement of muscular volume by the bioelectricity impedance measuring device related to an embodiment of the invention.

FIG. 8 is the graph which shows the correlation of the nutrient state which is measured by the MUAC method and Phase angle theta related to an embodiment of the invention.

FIGS. 10A, 10B, and 100 are graphs which show the relation of a girl's body composition and Phase angle theta related to the example of an embodiment of the invention.

DESCRIPTION OF THE PREFERRED EMBODIMENTS

Best Mode of Carrying Out the Invention

Embodiment

The suitable embodiment of this invention is described based on a drawing in the following.

At first, the embodiment of the measurement of malnutrition by the bioelectricity impedance measurement concerning an embodiment of the invention is described.

Figure 1:
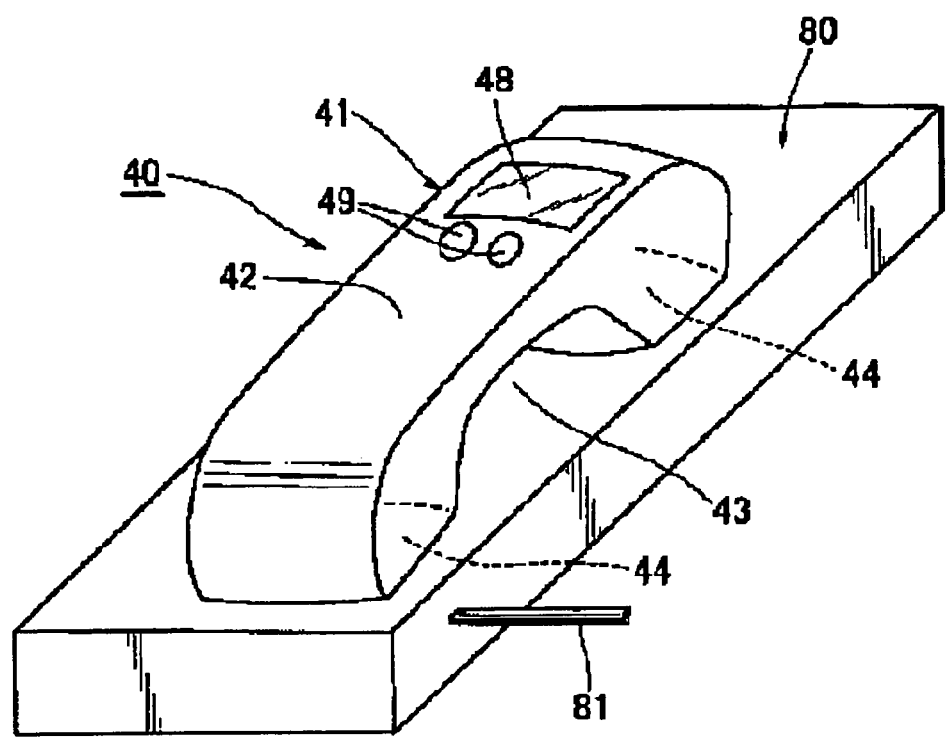
FIG. 1 is a perspective view showing the external component of the bioelectricity impedance measuring device related to an embodiment of the invention from the front side.

FIG. 1 is a perspective view showing external composition of a bioelectricity impedance measuring device involving an embodiment of the invention from a front side.

Figure 2:
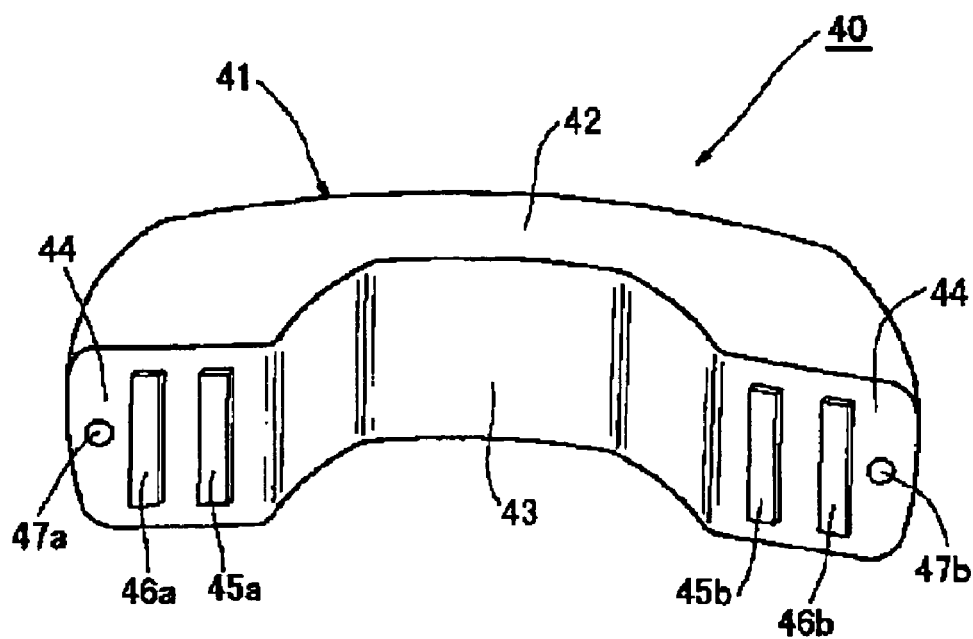
FIG. 2 is a perspective view showing the external component of the bioelectricity impedance measuring device as shown in FIG. 1 from the other side.

FIG. 2 is a perspective view showing external composition of a bioelectricity impedance measuring device shown in FIG. 1 from the behind side.

Figure 3:
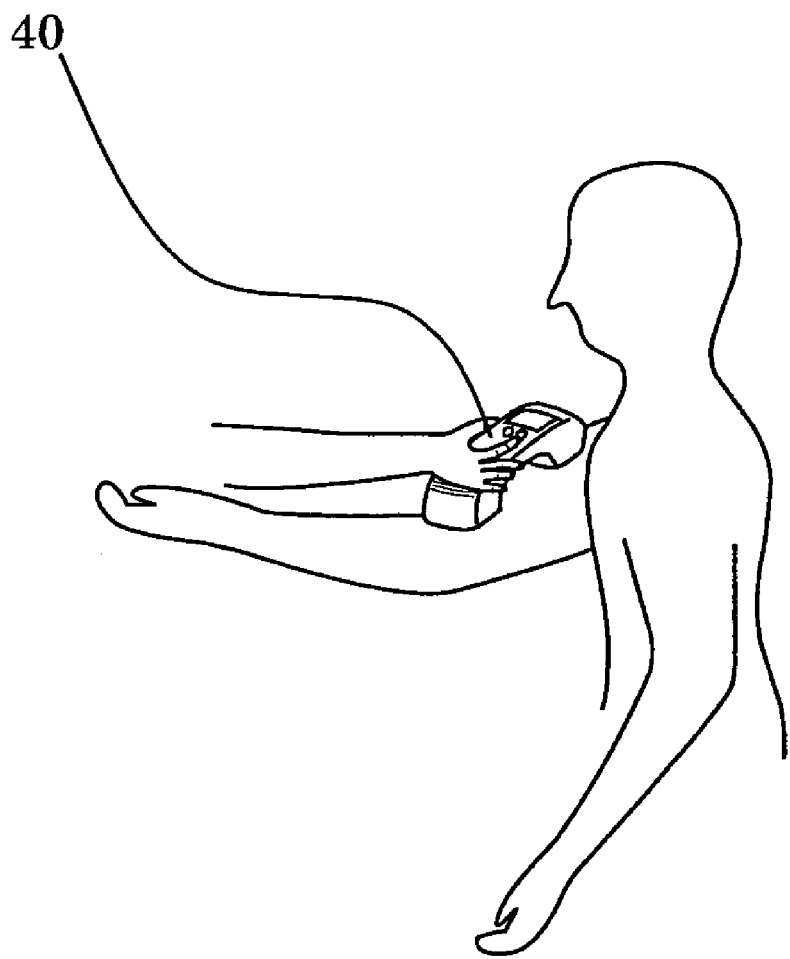
FIG. 3 is a perspective view showing indications that bioelectricity impedance is measured by using the bioelectricity impedance measuring device as shown in FIG. 1.

FIG. 3 is a perspective view showing indications that bioelectricity impedance is measured by using a bioelectricity impedance measuring device as shown in FIG. 1.

As shown in FIG. 3, this measuring device 40 is grasped by single hand and put to an upper arm part, and it measures bioelectricity impedance; and it is similar to a receiver of deferred type telephone provided with cylindrical gripper 42 which has the sectional shape of about square shapes, and two spurs which distort from both ends of gripper 42, project to a uniform direction, and have a contact surface so that concave 43 being formed with gripper 42.

(External Component of a Bioelectricity Impedance Measuring Device)

As shown in FIGS. 1 and 2, this measuring device 40 is provided with almost palm-sized housing 41 with carrying by single hand easily.

Housing 41 is provided with contact surface 44 put to an upper arm part and gripper 42 grasped by a single hand. Contact surface 44 is equipped fixedly with one pair of cylindrical voltage measurement electrodes 45a and 45b and one pair of cylindrical measuring-electric-current applicators 46a and 46b which are prolonged along contact surface 44 so that each may intersect perpendicularly to a longer direction of housing 41, and one pair of circular electrodes 47a and 47b for charge.

One pair of measuring-electric-current applicators 46a and 46b are located so that one pair of voltage measurement electrodes 45a and 45b may be inserted in between, and one pair of electrodes 47a and 47b for charge are located so that one pair of voltage measurement electrodes 45a and 45b and one pair of measuring-electric-current applicators 46a and 46b may be inserted.

These three pairs of electrodes 47a, 46a, 45a, 45b, 46b, and 47b are located so that it may line up almost linear with a longer direction of housing 41.

It is formed so that gripper 42 may be made into a form to be easily grasped by a single hand.

In a surface of the opposite side of contact surface 44 of housing 41, it is provided with display screen 48 (display) which is a liquid crystal display, or an organic electroluminescence display or the like, with which operation guidance, a measuring situation, a test result, a calculated result, or the like, are displayed, and operation key 49 for inputting a control instruction of this measuring device 40, an individual parameter of measuring person required for measurement, or the like.

This measuring device 40 is charged by performing contact surface 44 toward the bottom, putting this measuring device 40 on a predetermined position of charger 80, and contacting one pair of electrodes, 47a and 47b, for charge to one pair of electrodes corresponding to these (not shown), which is equipped in charger 80.

Charger 80 is provided with AC cord 81. Although not illustrated, a plug, which can be plugged into an electric socket of the usual household power supply, is attached at an end of AC cord 81.

(Internal Configuration)

Figure 4:
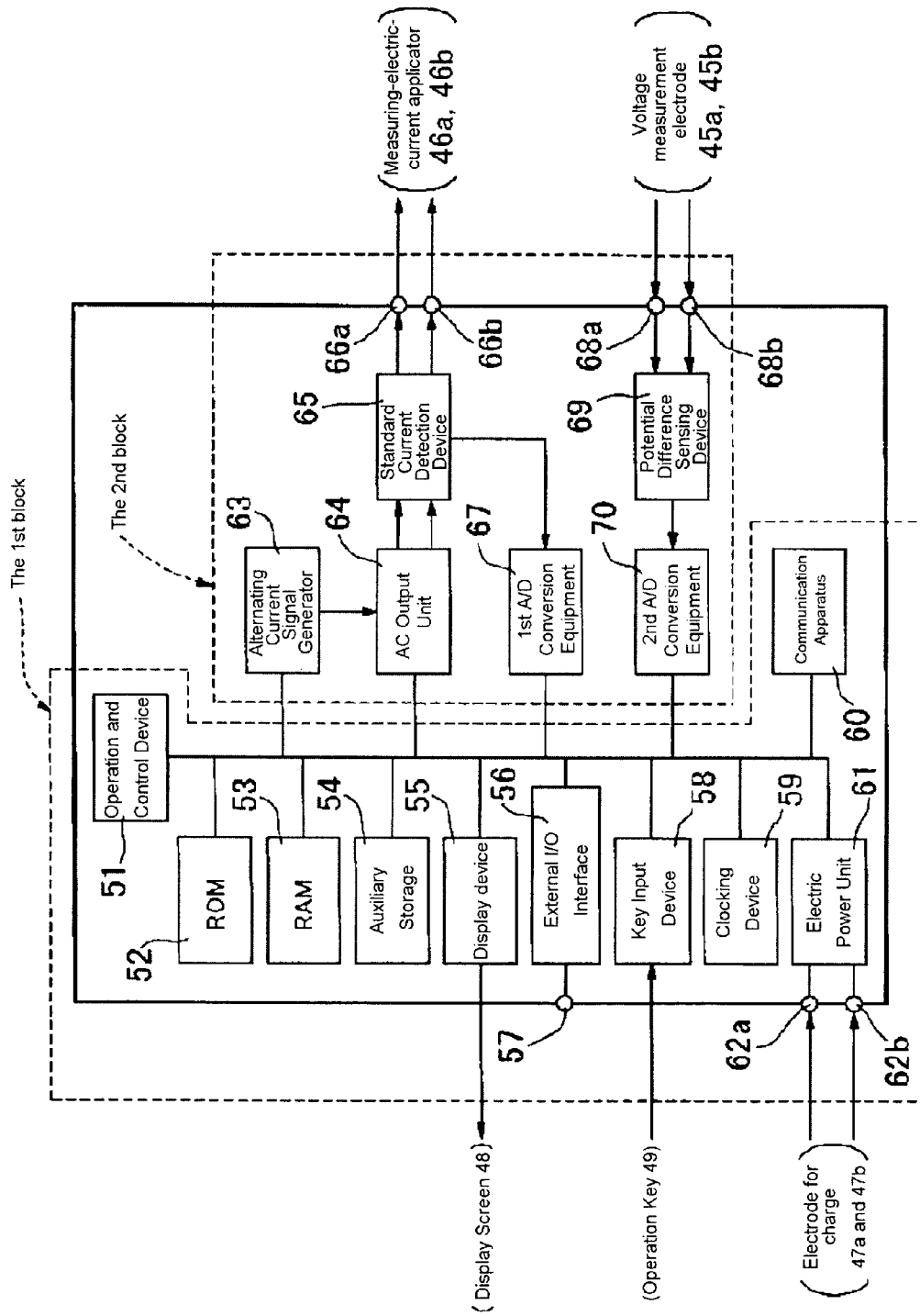
FIG. 4 is a block diagram showing the internal configuration of the bioelectricity impedance measuring device as shown in FIG. 1.

FIG. 4 is a control block diagram showing an internal configuration of a bioelectricity impedance measuring device as shown in FIG. 1 to FIG. 3.

As shown in FIG. 4, an internal configuration of this measuring device 40 is divided into the 1st block that mainly carries out control, operation, and an input/output of data, and the 2nd block that mainly carries out bioelectricity impedance measurement and conversion to a digital signal from an analog signal; and these blocks are stored in housing 41.

The 1st block comprises the following:

Operation and control device 51, which carries out control about measurement, processing of measurement data, or the like;

ROM52 which memorizes control and a program for operation, malnutrition measurement program 200 used by this embodiment, muscular volume measurement program 210, a data table, regression, a constant, or the like;

RAM53 which memorizes temporarily measurement data, a calculated result, data read from the outside, a program, or the like;

Auxiliary storage 54 which is a nonvolatile flash memory, SRAM, or the like, and is able to memorize, read-out, and update about measurement data, a calculated result, and a parameter about an measurement, or the like;

Display 55 which is connected to display screen 48 and display screen 48 being made to display operation guidance, a measuring situation, a test result, a calculated result, or the like;

External I/O interface 56 which outputs a parameter about measurement, a test result, or the like, to an external device, and reads a parameter about measurement, control information at the time of measurement, a control program, or the like, into this measuring device 40 from an external device;

External interface terminal 57 which is for connecting external I/O interface 56 and an external device; Key input device 58 which is connected to operation key 49 and generates input, such as a control instruction of this measuring device 40, and an individual parameter of measuring person required for measurement, in response to a push-down of operation key 49;

Clocking device 59 which obtains an hour entry for managing time of measurement, or the like;

Communication apparatus 60 which transmits and receives a measured value and a parameter, or the like, computed from the measured value among other computers via a telephone line or LAN (local area network), or by using wireless communications of wireless LAN, Bluetooth (registered trademark), and a radio USB or the like;

Electric power unit 61 which is charged via one pair of electrodes, 47*a* and 47*b*, for charge, or starts or suspends an electric power supply to each part of this measuring device 40 by receiving input generated in key input device 58 by push-down of operation key 49; and Terminals 62*a* and 62*b* for charge, which connect one pair of electrodes, 47*a* and 47*b*, for charge, and electric power unit 61.

The 2nd block comprises the following:

Alternating current signal generator 63 which generates an alternating current signal of frequency arranged by a control program memorized by ROM52 or RAM53;

AC output unit 64 which makes an alternating current signal outputted from alternating current signal generator 63 into an alternating current signal of an effective value decided by a control program memorized by ROM52 or RAM53;

Standard current detection device 65 which detects current, which flows through measuring person, and is outputted as a standard current detecting signal;

One pair of AC output terminals, 66*a* and 66*b*, which outputs AC, supplied via standard current detection device 65 from AC output unit 64. The 1st A/D conversion equipment 67 which changes an analog signal, which is an output of standard current detection device 65, into a digital signal; One pair of voltage measurement terminals 68*a* and 68*b* which inputs two potential signals of measuring person;

Potential difference sensing device 69 which outputs a differential signal of a potential signal between one pair of voltage measurement terminals, 68*a* and 68*b*; and the 2nd A/D conversion equipment 70 which changes an analog signal, which is an output of potential difference sensing device 69, into a digital signal.

One pair of AC output terminals 66*a* and 66*b* are connected to one pair of measuring-electric-current applicators, 46*a* and 46*b*, and one pair of voltage measurement terminals 68*a* and 68*b* are connected to one pair of voltage measurement electrodes 45*a* and 45*b*.

[Measurement of Malnutrition]

Figure 5:
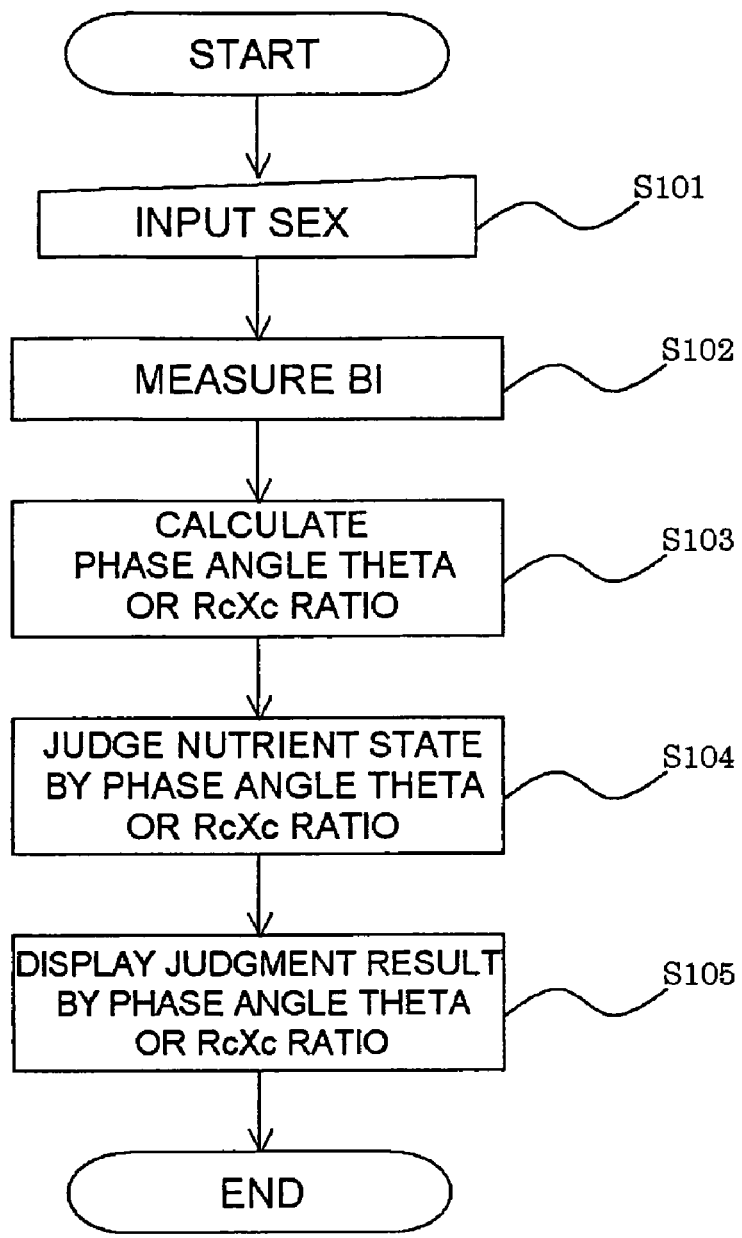
FIG. 5 is a flow chart in which an outline of the measurement procedure of the malnutrition and an operation by the bioelectricity impedance measuring device as shown in FIG. 1.

A measurement procedure of a bioelectricity impedance measuring device and an outline of operation, which were shown in FIG. 2, and measurement of malnutrition related to an embodiment of the invention are explained with reference to FIG. 5 which is a flow chart.

At first, when the person measuring carries out the push-down of the operation key 49, initialization of this measuring device 40 inner part is carried out, and an initial screen which is not illustrated is displayed on display screen 48.

(Step S101)

Then, in Step S101, the person measuring or a person being measured inputs the sex of a the person being measured, which is an individual parameter.

Operation key 49 may be equipped with a specific sex button about an input of sex.

About this data of sex, operation and control device 51 memorize to RAM53.

(Step S102)

Then, in Step S102, with directions of the person measuring or the person being measured, operation and control device 51 is interlocked with the mechanism of the 2nd block and measures bioelectricity impedance (BI: Bioelectric Impedance).

Here, as shown in FIG. 3, the person measuring grasps the measuring device 40 (when the person being measured measures by himself, it is a single hand), puts contact surface 44 to an upper arm part of the person being measured, and contacts two pairs of electrodes, 46*a*, 45*a*, 45*b*, and 46*b*, to an upper arm part of the person being measured.

And according to a display of display screen 48, operation key 49 is pressed by a fingertip of the hand which is grasping the measuring device 40, and directions of a measurement start are inputted.

Because this measuring device 40 is almost palm size which can be carried by a single hand easily and is provided with gripper 42 which is made into a form easily to be gasped by a single hand, the person measuring can grasp the measuring device 40 by single hand very easily by applying finger(s) to concave 43.

An input of directions of a measurement start will measure bioelectricity impedance as follows in Step S102.

Firstly, output signal frequency is set to alternating current signal generator 63 based on gauge control parameters (frequency, voltage, or the like) memorized to ROM 52 previously, or memorized to RAM 53 from auxiliary storage 54 or external I/O interface 56; and an output signal from alternating current signal generator 63 is outputted to AC output unit 64.

Then, based on a gauge control parameter, an output current value is set as a constant current output circuit of AC output unit 64. An output from AC output unit 64 passes sequentially to standard current detection device 65, one pair of AC output terminals 66*a* and 66*b*, and one pair of measuring-electric-current applicators 46a and 46b; and they are applied to the person being measured. At this time, current which flows into the person being measured is detected by the standard current detection device 65, and an output of that analog signal is converted into a digital signal by the 1st A/D conversion equipment 67.

Then, an output of the digital signal is memorized to RAM 53.

Simultaneously, two potential signals of the person being measured pass one pair of voltage measurement electrodes 45a and 45b, and one pair of voltage measurement terminals 68a and 68b sequentially, and they are inputted into potential difference sensing device 69; and by potential difference sensing device 69, a differential signal of an inputted potential signal is outputted to the 2nd A/D conversion equipment 70.

In the 2nd A/D conversion equipment 70, the differential signal, which is an analog signal, is changed into a digital signal, and an output of the digital signal is memorized to RAM 53.

Thus, based on a gauge control parameter, duplicate measurement of the bioelectricity impedance is carried out for frequency Fi (i=1, 2, . . . , n).

Then, from bioelectricity impedance measured value, measured at Step S102, a bioelectricity impedance vector locus and parameter(s) about it is computed.

Figure 11:
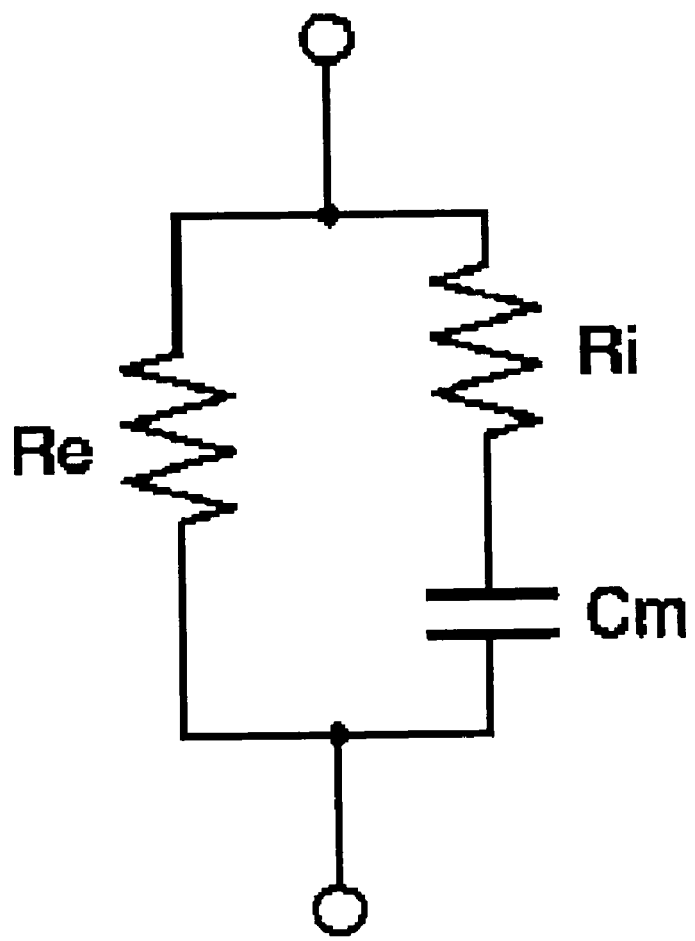
FIG. 11 is a representative circuit schematic showing bioelectricity impedance.

Usually, as shown in FIG. 11, although bioelectricity impedance is expressed in an equivalent circuit which is described as concentrated constant for extracellular fluid resistance Re, intracellular fluid resistance Ri, and cell membrane capacity Cm, in fact, since each cell comprising a living body is expressed in a circuit having different constants, respectively, by the difference in form and character, in a living body which is the aggregate, a bioelectricity impedance vector locus does not serve as a semicircle, for example, at the time of measuring an equivalent circuit by a concentrated constant, it is supposed that it will become a circle according to a Cole-Cole circular arc law.

Figure 12:
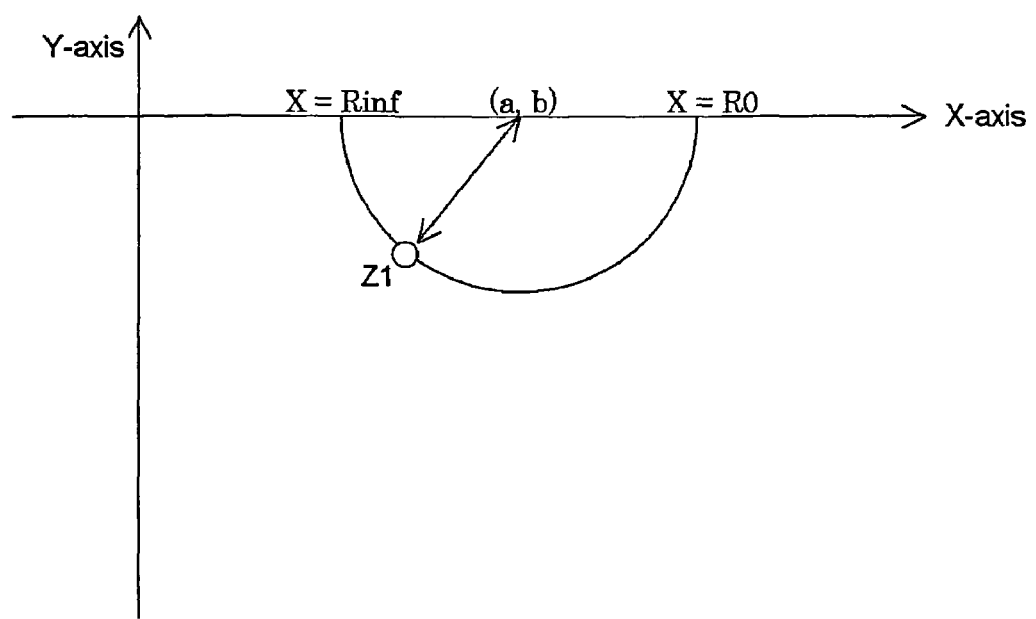
FIG. 12 is the graph charts showing a bioelectricity impedance vector locus.

Therefore, generally, bioelectricity impedance draws a circular locus as shown in FIG. 12.

Here, the X-axis shows a resistance component of bioelectricity impedance, and the Y-axis shows a reactance component of bioelectricity impedance.

Because a reactance component of bioelectricity impedance is capacitive and shows a negative value, a bioelectricity impedance vector locus is located under the X-axis; and from the assumption that a bioelectricity impedance vector locus for determining is a circle, in each of Frequency F1, F2, . . . , FN, bioelectricity impedance measured value Z1, Z2, . . . , ZN is on the circumference of a certain circle.

Here, when the X coordinate of the center of a circle is "a," the Y coordinate of the center of the circle is "b," the radius of the circle is "r," an equation of a circle which passes along bioelectricity impedance measured value is shown such as equation 1.

$(X-a)^2+(Y-b)^2=r^2$ (equation 1)

"a," "b," and "r" is determined by substituting bioelectricity impedance measured value Z1, Z2, . . . , ZN for frequency F1, F2, . . . , FN, to equation 1.

Also, X is shown by equations 1 as follows.

$X=a+\text{sqrt}(r^2-b^2)$ (equation 2)

sqrt( ) shows a square root.

Also, intersection of a circle and the X-axis, R0 and Rinf (R0>Rinf), expressed with equation 1, are calculated as follows by equation 2.

$R0=a+\text{sqrt}(r^2-b^2)$ (equation 3)

$R\text{inf}=a-\text{sqrt}(r^2-b^2)$ (equation 4)

Re and Ri in the equivalent circuit of FIG. 11 are calculated as follows by equation 3 and equation 4.

$Re=R0.$ (equation 5)

$Ri=R0*R\text{inf}/(R0-R\text{inf}).$ (equation 6)

Because bioelectricity impedance vector Zc in characteristic frequency Fc is the point that an absolute value of a reactance component, that is the Y axial component, becomes the maximum, the X coordinate value, which is a resistance component in that case, and the Y coordinate value, which is reactance components, are computed as follows.

$X=a.$ (equation 7)

$Y=b-r$ (equation 8)

Here, when Rc is a resistance component of Zc, and Xc is a reactance component of Zc, Zc is shown as follows.

$Zc=Rc+j*Xc=a+j*(b-r)$ (equation 9)

Also, when Z (omega) is a bioelectricity impedance vector in omega and tau and beta are constants, by Cole-Cole circular arc law, the bioelectricity impedance vector in any circular frequency omega is shown as follows.

$Z(\text{omega})=(R0-R\text{inf})/\{1+(j*\text{omega}*\text{tau})*\text{beta}\}$ (equation 10)

Equation 10 is shown as follows as tau=1/omega*c.

$Z(\text{omega})=(R0-R\text{inf})/\{1+((j*\text{omega})/(\text{omega}*c))$
$*\text{beta}\}$ (equation 11)

Here, since omega*c=2*pi*Fc, Fc and beta are determined by using bioelectricity impedance measured value measured previously.

As mentioned above, based on the bioelectricity impedance vector locus, which is calculated from bioelectricity impedance measured value, the parameter about it, which are R0, Rinf, Re, and Ri, Zc, Rc, Xc, Fc, or the like, the amounts of body compositions, such as extracellular fluid volume, intracellular fluid volume, body water volume (sum of extracellular fluid volume and intracellular fluid volume), amount of body fat, and a fat-free mass (difference of weight and amount of body fat), are computed; and also, from the computed amount of body compositions, ratio of Intracellular fluid volume versus extracellular fluid volume, ratio of extracellular fluid volume versus body water volume, dehydration state determined by body water volume ratio, ratio of body fat, or the like, are computable.

(Step S103)

Then, in Step S103, in order to measure malnutrition related to an embodiment of the invention, By malnutrition measurement program 200 (malnutrition measuring means) memorized in ROM52, operation and control device 51 compute, for example, the value called Phase angle theta or a RcXc ratio from an above-mentioned parameter (R0 . . . Fc, or the like).

Hereafter, operation and control device 51 execute malnutrition measurement program 200 to Step S105.

It turns out that Phase angle theta and the RcXc ratio can measure a state of malnutrition correlated with acute malnutrition.

As explained with reference to FIG. 8, an upper arm circumference measured by the above-mentioned MUAC method, which is the X-axis, and Phase angle theta, which is Y-axes, show extremely good correlation of R=0.901 and P<0.001.

Here, Phase angle theta, related to an embodiment of the invention, is computed by the following equation from above-mentioned Rc and Xc.

$$\text{Theta} = a\tan(Xc/Rc) * 180/pi \quad \text{(equation 12)}$$

atan( ) is a function which determines an angle of a radian unit by arc tangent.

In order to use a nutrient state criterion simpler, the following RcXc ratio eta is computable with the following equations.

$$Eta = Xc/Rc \quad \text{(equation 13)}$$

(Step S104)

Then, operation and control device 51 judge a nutrient state by Phase angle theta or RcXc ratio eta calculated at Step S103.

Here, in an embodiment of the invention, with regression which used positive correlation as shown in FIG. 8, values of Phase angle theta or values of RcXc ratio thetas and etas, which are equivalent to values of an upper arm circumference corresponding to several steps of states being from acute malnutrition with death possibility to normal, are memorized to a data table for malnutrition measurement program 200 in ROM52 as threshold value(s).

A nutrient state is judged by comparing value(s) of Phase angle theta or RcXc ratio eta calculated for measurement with threshold value thetas and etas for this data table.

Accordingly, an index showing directly whether malnutrition or not (normal state) can be obtained.

As referred to in FIG. 7, for example, because value thetas of Phase angle theta equivalent to an upper arm circumference of 14 cm, which is in a normal state, is 4, operation and control device 51 judges it as normal state, if a value of obtained Phase angle theta is four or more.

(Step S105)

Then, in Step S105, operation and control device 51 displays a result of a judgment of a nutrient state of Step S104 on display screen 48.

This is indicated, while displaying a value of Phase angle theta or RcXc ratio eta, for example, by drawing an indication of a green bar, and the indication which the person measuring can easily recognize, visually and intuitively, can be given.

As an example as shown in FIG. 7A, when it classifies by color and displays, such as, green as normal, yellow as risk of malnutrition, orange as malnutrition of a degree in the middle, red as serious malnutrition and danger with death, and it is suitable because the person measuring understands and interprets the indication easily.

For example, if a value of Phase angle theta is 2, since it is equivalent to malnutrition and is "there is danger of malnutrition", a yellow bar of display screen 48 can be turned on.

As the mechanism for urging cautions the person measuring when diagnosing many children {when it is "serious malnutrition and thus there is a danger of death" (it is equivalent to acute malnutrition)} which are extremely malnourished, it is also available to provide notification by using a buzzer, a sound effect, blinking of the drawn bar, or the like.

After a procedure of the above measurement is completed, the person measuring turns off the measuring device 40, and ends the measurement.

A test result of an above-mentioned nutrient state is printable with a printer, or the like, which are not illustrated; and also data of this test result is memorized to auxiliary storage 54, or it can read with a PC (personal computer), or the like, via communication apparatus 60. Since this data is, for example, a text file which tab-delimited, CSV (comma pause), or the like, which can be utilized without difficulty, it is useful for measurement of a plurality of children's malnutrition.

[Nutrition Evaluation and a Muscular Volume Display]

Figure 6:
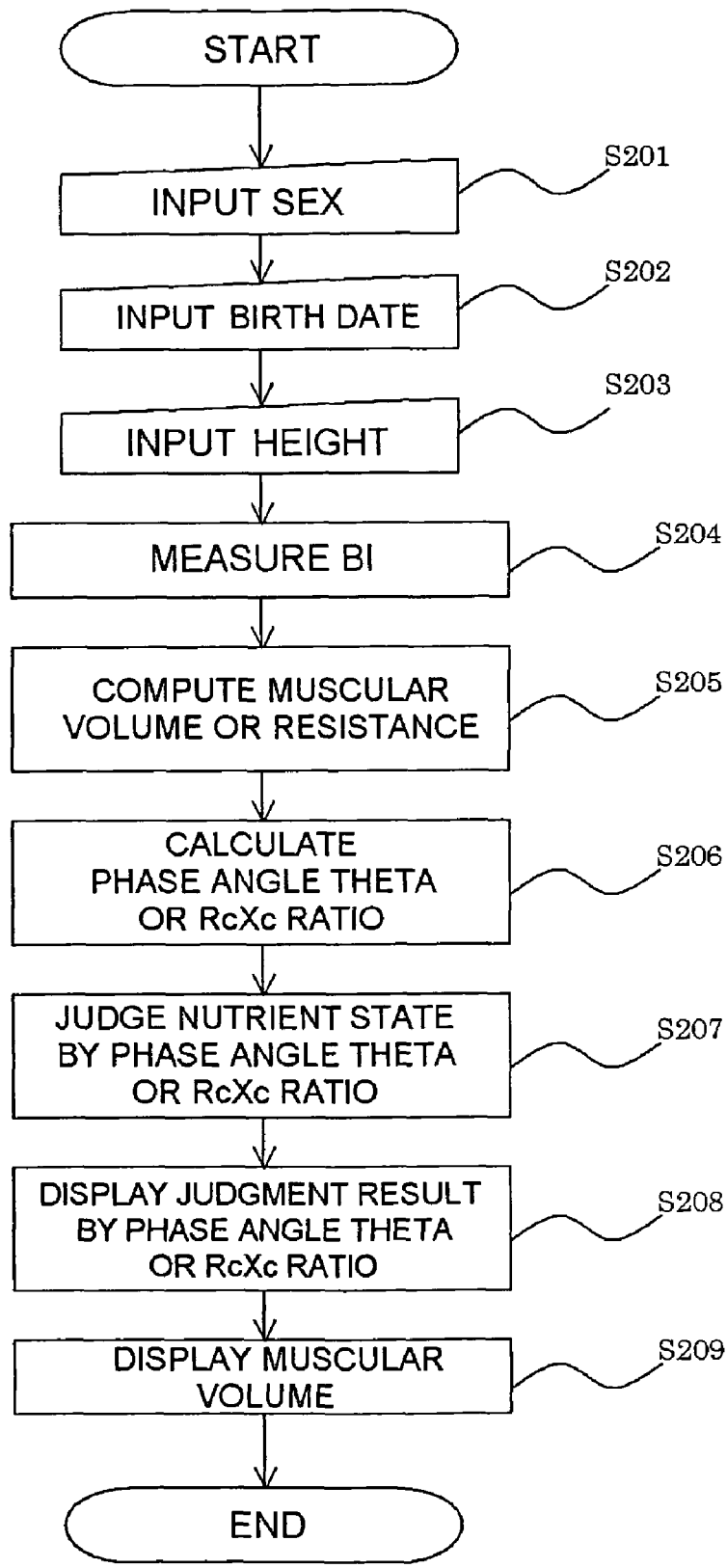
FIG. 6 is a flow chart in which an outline of the procedure of measurement of the malnutrition and muscular volume and operation by the bioelectricity impedance measuring device as shown in FIG. 1.

Subsequently, simultaneously with measurement of malnutrition related to an embodiment of the invention, when also displaying muscular volume, a measurement procedure and an outline of operation for this measuring device 40 are explained with reference to a flow chart of FIG. 6.

At first, it is the same as that of above-mentioned case where only measurement of malnutrition is carried out: when a person being measured carries out the push-down of the operation key 49, initialization of this measuring device 40 inner part is carried out, and the initial screen, which is not illustrated, is displayed on display screen 48.

(Step S201)

Then, in Step S201, the person measuring or the person being measured inputs the sex of the person being measured which is an individual parameter as well as above-mentioned step S101.

(Step S202)

Subsequently, in Step S202, the person measuring or the person being measured inputs the birth date of the person being measured.

This is because the birth date (age) information of the person being measured, which is an individual parameter, is required in order to compute the muscular volume.

(Step S203)

Then, in Step S203, the person measuring or the person being measured inputs the height of the person being measured. This is because the height information, which is an individual parameter, is also required to calculate the muscular volume.

About height, a result of the height measurement of a height scale, which is not illustrated, may be inputted via communication apparatus 60.

About the above individual parameters, the operation and control device 51 memorize to RAM 53.

The object transmitted from PC is also memorizable to RAM 53 via communication apparatus 60.

(Step S204)

Then, in Step S204, the person measuring or the person being measured measures bioelectricity impedance (BI) as like Step S102.

As mentioned above, based on a bioelectricity impedance vector locus which is calculated from bioelectricity impedance measured value and parameter about it, R0, Rinf, and Re, with Ri, Zc, Rc, Xc, Fc, or the like, it is computed from the amounts of body compositions, such as extracellular fluid volume, intracellular fluid volume, body water volume (sum of extracellular fluid volume and intracellular fluid volume), amount of body fat, and a fat-free mass (difference of weight and amount of body fat); and from the computed amounts of body compositions, Intracellular-fluid-volume versus extra-cellular-fluid-volume ratio, Extracellular-fluid-volume versus body water volume ratio, Dehydration determined by a body water volume ratio, a ratio of body fat, or the like can be computed.

(Step S205)

Then, in Step S205, operation and control device 51 computes muscular volume or resistance by muscular volume measurement program 210 (muscular volume measuring means) in ROM52.

Figure 9A:
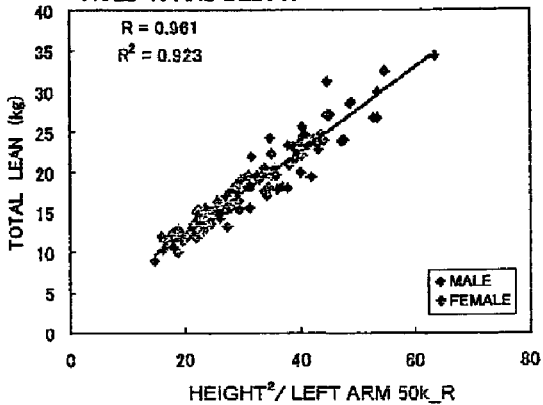
FIGS. 9A, 9B, and 9C are graphs which show correlation of impedance of the height$^2$/left arm and muscular volume of the whole body aged 10 and below and aged 60 and over, which is related to the embodiment of the invention.
Figure 9B:
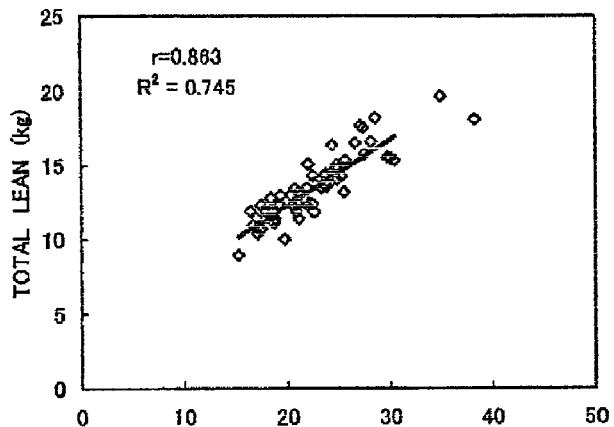
Figure 9C:
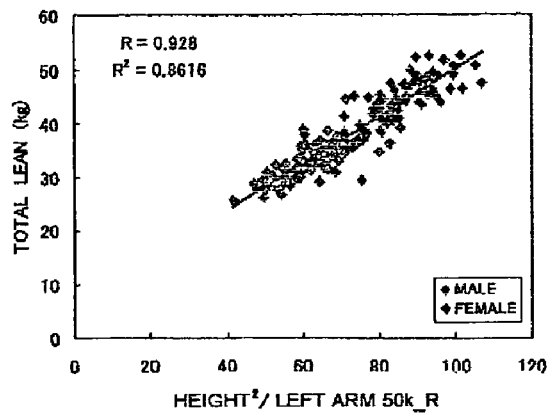

The artificer of this invention researches wholeheartedly, about calculation of muscular volume, as referred to FIG. 9, they ascertained that, a person being measured who is aged 10 or younger (a result is shown in FIG. 9A) or aged 60 or older (a result is shown in FIG. 9C), impedance of the height$^2$/left arm (or right arm), has strong correlation to muscular volume of the whole body.

It also turns out that especially a person being measured who is aged 5 or younger (a result is shown in FIG. 9B), impedance of the height$^2$/left arm (or right arm), has strong correlation to muscular volume of the whole body.

In this measuring device 40, regression or a data table by these correlations is memorized in ROM 52.

Thus, it enables to carry out measurement more exactly than the conventional MUAC method about a person being measured who is aged 5 or younger.

Measurement of muscular volume is also accurately available about a child who is aged 10 years old or younger in which age is older than 5 years old, and a person being measured who is aged 60 or older.

Further, because it also memorizes the regression of a person being measured who is older than 10 years old and who is younger than 60 years old, muscular volume can be measured for a person being measured of all these ages.

Because it is available to carry out exact measurement by bioelectricity impedance measurement, if a stable measurement posture can be taken, a newborn infant's muscular volume can be measured, even if the newborn is a premature baby, or the like.

In this case, a ratio of water content of the body changes according to age, since there are extremely high ratios of water content, especially among newborn infants, and reduction continues rapidly until about 1 years-old age, and it decreases gently after that, it can be measured more accurately by carrying out this compensation.

In the case of a newborn infant, since the hand and foot are bent, there is a problem that measurement of the exact bioelectricity impedance is difficult.

For this reason, it is preferred to measure while a newborn infant is asleep, or measuring the newborn infant's hand and foot when they are lengthened by a method such as using a weight of a sand bag in order to make he or she take a stable measurement posture.

About the calculation of muscular volume of an embodiment of the invention, a value of height$^2$/Zc is applied to the regression or the data table related to above-mentioned muscular volume, and it is computed as a LMI value (muscular volume/height$^2$).

Further, when a threshold value based on the above-mentioned graph is set up and is compared with this, by the LMI value, a judgment is carried out corresponding to muscular volume from "there is a little quite little muscular volume" to "normal."

Also, more simply, regression based on Rc of a person being measure aged 10 or younger and aged 60 or older is prepared; Rc, which is the measured value related to an embodiment of the invention, is applied; and a value of resistance equivalent to a LMI value may be computed.

(Step S206)

In Step S206, operation and control device 51 computes Phase angle theta or RcXc ratio eta by malnutrition measurement program 200 in ROM52 as like above-mentioned step S103.

(Step S207)

In Step S207, operation and control device 51 judges a nutrient state from Phase angle theta or RcXc ratio eta as like above-mentioned step S104.

(Step S208)

In Step S208, operation and control device 51 displays a value of Phase angle theta or a value of a RcXc ratio, and a result of a judgment of a nutrient state on display screen 48 as like Step S105.

(Step S209)

Then, in Step S209, operation and control device 51 displays muscular volume on display screen 48.

As refer to FIG. 7B, as well as an indication of a nutrient state at the same time of displaying a LMI value about muscular volume, for example, when a result of a judgment of a LMI value is displayed by corresponding to the case of "quite small" as in red, the case of "small" as in orange, the case of "slightly small" as in yellow, and the case of "normal" or more as in green.

In the "quite small" case, as like the display of nutrition evaluation, it is also available to tell the person measuring by a sound effect, blinking, or the like.

Confirming this result, the person measuring will turn off the measuring device 40, and end measurement.

A test result of this muscular volume, as well as a test result of above-mentioned malnutrition, can be transmitted to a PC or to a printer.

By comprising as mentioned above, with measuring device 40 related to an embodiment of the invention, bioelectricity impedance measurement can be carried out and Phase angle theta or a RcXc ratio can be measured.

Thereby, malnutrition can be measured excellently and repeatedly rather than the conventional MUAC method. Especially, if the length of an electrode section or a size of equipment is changed, for example, according to the person being measured, such as an infant or a 5 year old child, electrodes will be applied to the same position each time, and it can also be measured excellently and repeatedly.

It becomes available to obtain an exact measured result of malnutrition in high repeatability by measuring malnutrition with this measuring device 40 and the MUAC method at the same time.

In addition, since unlike a measuring device of conventional technology 1, this measuring device 40 is adjusting each datum in ROM 52 so that an electrode is applied to the upper arm part, higher correlation can be acquired with a result of the MUAC method, which a doctor follows as a standard.

In the case of a small child, since a lower arm is proportional to muscles of a hand, there is a tendency which increases more than bodily muscular volume.

However, it becomes available to measure a state of malnutrition more accurately by measuring the upper arm part.

Further, although it is described to be executed directly in the inside of ROM 52, malnutrition measurement program 200 and muscular volume measurement program 210 may be executed by being read in RAM 53.

This measuring device 40 can measure malnutrition regardless of a measurement posture (a standing position or a dorsal position).

For this reason, it can measure malnutrition of a person being measured who is in a bedridden state because of bad nutritional status.

In addition, malnutrition can be measured even in the case of a person being measured who is difficult to measure bioelectricity impedance because the heel is keratinized by the environment of living with bare feet, or the like, or by age.

Since a function that measures malnutrition is added to a small lightweight measuring device such as this measuring device 40, carrying is convenient.

Thereby, even in the land that has not developed transportation facilities or has suffered natural or human disasters, reproducible and exact malnutrition measurement can be carried out simply.

In addition, since this measuring device 40 can also be operated by a battery, which is not illustrated, it can be used also in a land where electricity has not become popular.

Even if it does not carry out inputs, such as height or weight, malnutrition can be measured easily in a short time by using Phase angle theta.

For this reason, when it is necessary to judge a nutrient state for many children, such as a refugee camp, it can use efficiently.

In addition, since this measuring device can be visually displayed intelligibly by displaying a judged result of a nutrient state with a bar, it becomes available to reduce the possibility that the person measuring will make a mistake about the result of malnutrition.

Because it also measures muscular volume based on height, it is available to measure a higher-precision of malnutrition.

EXAMPLES

Figure 10A:
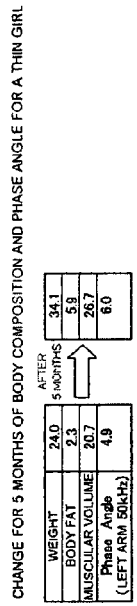
Figure 10B:
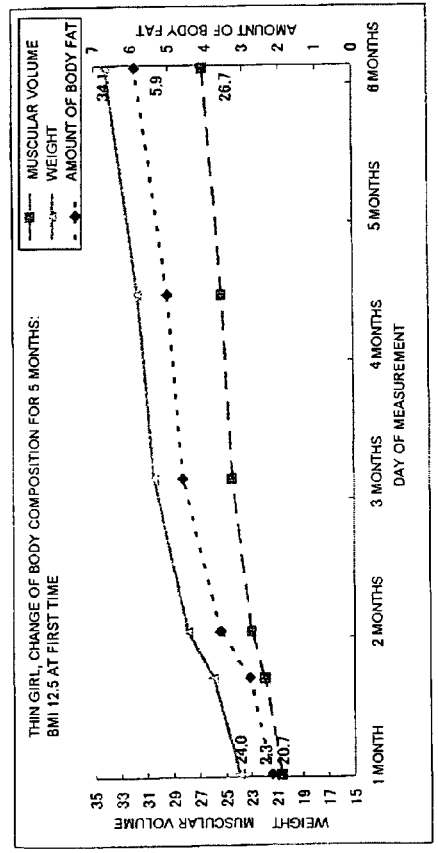

Subsequently, an example is described with reference to FIG. 10, where a value of Phase angle theta is actually measured with this measuring device 40 (a test result is shown in FIG. 100), and muscular volume with standard equipment is also measured as a comparison (a test result is shown in FIG. 10B).

Figure 10C:
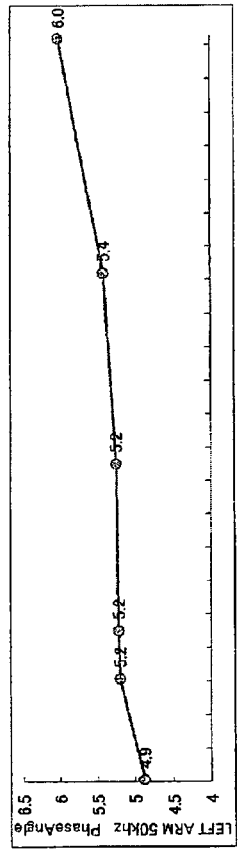

FIG. 10 shows a graph which shows change for five months of body composition and values of Phase angle theta for a girl who become thin by childcare abandonment.

In each graph, the horizontal axis shows time, and the vertical axis shows change of each value.

The girl has recovered to 34.1 kg in five months, although her weight was in the state of malnutrition medically, 24.0 kg on the first day of the measurement (a test result is shown in FIG. 10A).

Actually, it is known that recovering muscles earlier when recovering malnutrition.

It turns out that the value of Phase angle theta, of the lower graph, is also rising with the increase in the muscular volume of the upper graph.

Moreover, after definite recovery, a direction of an increase in fat tends to come earlier than an increase in muscular volume when not carrying out exercise or the like, and it turns out that a value of Phase angle theta is well coherent with an increase in muscular volume.

In addition, measurement of the state of the malnutrition by the value of Phase angle theta of this measuring device 40 is well coherent also with the medical view.

Thus, measuring device 40 applied to an embodiment of the invention can carry out sequential observation about the improvement of malnutrition.

This is because it can measure malnutrition with high repeatability and a subject's muscular volume can also be measured, simultaneously.

Therefore, it becomes available to perceive the recovery degree from malnutrition conveniently.

Since prescription can be considered by seeing a recovery degree as referred to the data, of measuring device 40, the burden of the person measuring or a doctor is reduced.

Also, this measuring device 40 can transmit the measured results to other computers which are not illustrated; the other computers are provided with a nonvolatile memory method, such as HDD which is an auxiliary storage; and for this reason, it can carry out checking data of this sequential observation conveniently. Further, since measurement of malnutrition is convenient, it is suitable for pursuing a change with time of a state of malnutrition, and since a numerical value can increase and it can be grasped visually with recovery, it is available to promote volition imposed on recovery of the person measuring or by recovery of the person being measured.

In addition, unlike the bioelectricity impedance measuring device of conventional technology 1, this measuring device 40 can be measured also about the muscular volume of a subject, including a child and an old person.

For this reason, it is enabled by measuring muscular volume, in addition to Phase angle theta, to grasp a restorative degree more accurately.

Since this measuring device 40 can perform measurements in a short time, it can measure malnutrition in infants, a person with a large body motion, and a person with an intense tremor (tremulus).

Actually, infants, an inpatient, a bedridden patient, anorexia nervosa, or the like, has a high possibility of falling into malnutrition and needs to asertain a nutrient state.

For this reason, in addition to measuring a body fat ratio or the like by, such as, the body composition monitor of conventional technology 1, this measuring device 40 which measures the exact high malnutrition of repeatability is effectively utilizable.

Furthermore, this measuring device 40 does not need special operation; and for this reason, anyone, such as parents, a caregiver, or a person being measured himself/herself, who is neither a nurse nor an inspecting engineer, can measure malnutrition.

In addition, because of small equipment, it can be used in various measuring situations, such as a hospital, a house, a medical checkup center, an elderly-people institution, and a child welfare institution.

It can be used at any time irrespective of a use situation; and thus, there is the feature that flexibility is high.

Although the thin patient with eating disorders, such as anorexia nervosa and anorexia nervosa, has recovered the state of malnutrition, he or she may feel that weight increases for fear, and there is a problem that he or she does not recover easily.

When using this measuring device 40 for such a patient, in order not to measure weight, it becomes available not to give an scary feeling and to recover the state of malnutrition smoothly.

The component and operation of the above-mentioned embodiment are an example, and it is needless to say that it can change suitably and can perform in the range which does not deviate from the purport of this invention.

What is claimed is:

1. A bioelectricity impedance measuring device, which comprises:
   a housing with a contact surface capable of being placed on a part of the body;
   a handheld gripper configured to be easily grasped;
   electrodes facing the same direction from the contact surface of the housing;
   an operation and control device configured to measure a state of malnutrition from a phase angle theta and/or an RcXc ratio eta by a malnutrition measurement program; and
   a display which shows the measured state of malnutrition,
   wherein the operation and control device is configured to store values of Phase angle theta and/or an RcXc ratio eta in a data table as threshold values of Phase angle theta and/or values of RcXc ratio eta to measure a state of malnutrition from Phase angle theta and/or an RcXc ratio eta,
   wherein the values of Phase angle theta and/or RcXc ratio eta are equivalent to values of an upper arm circumference corresponding to several states of malnutrition determined by the Mid-Upper Arm Circumference (MUAC) method, and
   wherein the operation and control device thereby is configured to measure a state of malnutrition by comparing values of Phase angle theta and/or RcXc ratio eta calculated from measurement with the threshold values of Phase angle theta and/or RcXc ratio eta stored in the data table.

2. The bioelectricity impedance measuring device according to claim 1, wherein
   the gripper forms a concave surface, and
   the electrodes facing from the contact surface are located at both ends of the concave surface of the gripper.

3. The bioelectricity impedance measuring device according to claim 1, wherein the display shows a color-coded indication of a judged result of the state of malnutrition with a bar classified by color,
   wherein the display is configured to provide a numerical value of the state of malnutrition along with the color-coded indication of the state of malnutrition, and
   wherein the display is configured to include a further notification to warn of serious malnutrition and thus a danger of death when an acute state of malnutrition has been measured.

4. The bioelectricity impedance measuring device according to claim 1, wherein
   the operation and control device is configured to further measure muscular volume by a muscular volume measuring program.

5. The bioelectricity impedance measuring device according to claim 4, wherein
   the operation and control device is configured to measure muscular volume for a child aged 5 or younger or an adult aged 60 or older, the operation and control device being provided with at least one of data from the data table or regression analysis.

6. The bioelectricity impedance measuring device according to claim 4, wherein
   the operation and control device is configured to measure a state of malnutrition and/or measure a muscular volume by individual parameters with sex, height and age.

7. The bioelectricity impedance measuring device according to claim 1, wherein
   the operation and control device is configured to measure the state of malnutrition with the device being portable.

8. A malnutrition measurement system, comprising:
   a bioelectricity impedance measuring device provided with
      a housing with a contact surface capable of being placed on a part of the body,
      a handheld gripper which is configured to be easily grasped,
      electrodes facing the same direction from the contact surface of the housing, and
      an operation and control device configured to measure a state of malnutrition from a phase angle theta and/or an RcXc ratio eta by a malnutrition measurement program; and
   a computer provided with an auxiliary storage which is operative to receive data from the bioelectricity impedance measurement device, and operative to memorize sequential data via communication,
   wherein the operation and control device is configured to store values of Phase angle theta and/or an RcXc ratio eta in a data table as threshold values of Phase angle theta and/or values of RcXc ratio eta to measure a state of malnutrition from Phase angle theta and/or an RcXc ratio eta,
   wherein the values of Phase angle theta and/or RcXc ratio eta are equivalent to values of an upper arm circumference corresponding to several states of malnutrition determined by the Mid-Upper Arm Circumference (MUAC) method, and
   wherein the operation and control device thereby is configured to measure a state of malnutrition by comparing values of Phase angle theta and/or RcXc ratio eta calculated from measurement with the threshold values of Phase angle theta and/or RcXc ratio eta stored in the data table.

9. A malnutrition measuring method, comprising:
   measuring a state of malnutrition from Phase angle theta and/or an RcXc ratio eta with a portable, handheld electrical impedance measuring device which is configured to be placed in contact with an upper arm;
   measuring muscular volume by Phase angle theta and/or an RcXc ratio eta; and
   showing on a display the results of the measurements of the state of malnutrition and the muscular volume, the display providing a numerical value of each of the state of malnutrition and the muscular volume along with a color-coded indication of each of the state of malnutrition and the muscular volume, and also providing a further notification to warn of serious malnutrition and thus a danger of death when an acute state of malnutrition has been measured,
   wherein the measuring a state of malnutrition further comprises:
      storing values of Phase angle theta and/or an RcXc ratio eta in a data table as threshold values of Phase angle theta or values of RcXc ratio eta to measure a state of malnutrition from Phase angle theta and/or an RcXc ratio eta, wherein the values of Phase angle theta and/or RcXc ratio eta are equivalent to values of an upper arm circumference corresponding to several states of malnutrition determined by the Mid-Upper Arm Circumference (MUAC) method; and
      comparing values of Phase angle theta and/or RcXc ratio eta calculated from measurement with the threshold values of Phase angle theta and/or RcXc ratio eta stored in the data table to thereby measure a state of malnutrition.

10. A portable, handheld malnutrition measuring device, which is an electrical impedance measuring device, comprising:
- an operation and control device configured to measure bioelectricity impedance at an upper arm, the operation and control device further configured to measure a state of malnutrition from Phase angle theta and/or an RcXc ratio by values of the bioelectricity impedance,
- wherein the operation and control device is configured to store values of Phase angle theta and/or an RcXc ratio eta in a data table as threshold values of Phase angle theta and/or values of RcXc ratio eta to measure a state of malnutrition from Phase angle theta and/or an RcXc ratio eta,
- wherein the values of Phase angle theta and/or RcXc ratio eta are equivalent to values of an upper arm circumference corresponding to several states of malnutrition determined by the Mid-Upper Arm Circumference (MUAC) method, and
- wherein the operation and control device thereby is configured to measure a state of malnutrition by comparing values of Phase angle theta and/or RcXc ratio eta calculated from measurement with the threshold values of Phase angle theta and/or RcXc ratio eta stored in the data table.

11. A malnutrition measuring method, comprising:
- measuring a state of malnutrition from Phase angle theta and/or an RcXc ratio with a portable, handheld electrical impedance measuring device which is configured to be placed in contact with an upper arm; and
- showing on a display the result of measurement by the state of malnutrition,
- wherein the measuring a state of malnutrition further comprises:
  - storing values of Phase angle theta and/or an RcXc ratio eta in a data table as threshold values of Phase angle theta or values of RcXc ratio eta to measure a state of malnutrition from Phase angle theta and/or an RcXc ratio eta, wherein the values of Phase angle theta and/or RcXc ratio eta are equivalent to values of an upper arm circumference corresponding to several states of malnutrition determined by the Mid-Upper Arm Circumference (MUAC) method; and
  - comparing values of Phase angle theta and/or RcXc ratio eta calculated from measurement with the threshold values of Phase angle theta and/or RcXc ratio eta stored in the data table to thereby measure a state of malnutrition.

* * * * *